United States Patent
Kensy et al.

(10) Patent No.: US 10,406,265 B2
(45) Date of Patent: Sep. 10, 2019

(54) METHOD AND DEVICE FOR ISOLATING TISSUE CELLS FROM A LIQUID

(75) Inventors: Arnd Kensy, Michendorf (DE);
Konrad-Wenzel Winkler, Warin (DE);
Klaus Ueberreiter, Birkenwerder (DE)

(73) Assignee: HUMAN MED AG, Schwerin (DE)

(*) Notice: Subject to any disclaimer, the term of this patent is extended or adjusted under 35 U.S.C. 154(b) by 1229 days.

(21) Appl. No.: 12/996,397

(22) PCT Filed: May 29, 2009

(86) PCT No.: PCT/DE2009/000775
§ 371 (c)(1),
(2), (4) Date: Dec. 6, 2010

(87) PCT Pub. No.: WO2009/149691
PCT Pub. Date: Dec. 17, 2009

(65) Prior Publication Data
US 2011/0104800 A1 May 5, 2011

(30) Foreign Application Priority Data
Jun. 10, 2008 (DE) .......... 10 2008 027 486

(51) Int. Cl.
  *C12N 5/07* (2010.01)
  *C12M 1/00* (2006.01)
  *A61M 1/00* (2006.01)
  *A61B 17/3203* (2006.01)

(52) U.S. Cl.
  CPC ........ *A61M 1/0001* (2013.01); *A61M 1/0056* (2013.01); *A61B 17/3203* (2013.01); *A61M 2202/08* (2013.01)

(58) Field of Classification Search
  CPC ............. A61M 1/0001; A61M 1/0056; A61B 17/3203

(Continued)

(56) References Cited

U.S. PATENT DOCUMENTS

| 4,228,798 A | 10/1980 | Deaton |
| 4,460,361 A | 7/1984 | Michals |

(Continued)

FOREIGN PATENT DOCUMENTS

| DE | 600 32 008 T2 | 6/2007 |
| EP | 1 234 589 A1 | 8/2002 |

(Continued)

OTHER PUBLICATIONS

U.S. Appl. No. 12/996,397, portion of final Office Action dated Dec. 10, 2015, 6 pages.*

(Continued)

*Primary Examiner* — Bobby Ramdhanie
*Assistant Examiner* — Denise R. Anderson
(74) *Attorney, Agent, or Firm* — Norris McLaughlin, P.A.

(57) ABSTRACT

A method and device for isolating tissue cells from a liquid is provided for integrating a mixture of the tissue cells and the liquid into a vacuum stream and isolating again from the vacuum stream in a tissue collection container (13). The tissue cells are filtered out of the mixture by means of gravity and the remaining liquid is re-integrated into the vacuum stream. In order to further develop said method and device to improve the care of the tissue cells and to reduce the filtration time, the vacuum stream that is isolated from the mixture inside the tissue collection container (13) is temporarily interrupted in order to generate a pressure that also acts on the mixture. In terms of the device, the connection between the lower collection chamber (23) for the liquid and the upper vacuum chamber (25) is formed by a blockable bypass line (27).

12 Claims, 3 Drawing Sheets

(58) Field of Classification Search
USPC .................................................... 435/308.1
See application file for complete search history.

(56) References Cited

U.S. PATENT DOCUMENTS

| | | | |
|---|---|---|---|
| 4,681,571 A | | 10/1987 | Nehring |
| 5,108,381 A | * | 4/1992 | Kolozsi ............... A61M 1/0056 210/406 |
| 5,720,299 A | * | 2/1998 | Theodoru .......... A61B 10/0291 600/573 |
| 6,071,095 A | * | 6/2000 | Verkaart ................... A61J 1/05 210/416.1 |
| 6,264,890 B1 | * | 7/2001 | Boehringer et al. ............ 422/44 |
| 6,589,219 B1 | * | 7/2003 | Shibuya ........................ 604/319 |
| 6,733,664 B2 | * | 5/2004 | Menne et al. ................ 210/110 |
| 2003/0042187 A1 | | 3/2003 | Menne |
| 2005/0139532 A1 | | 6/2005 | Hershberger |

FOREIGN PATENT DOCUMENTS

| | | |
|---|---|---|
| WO | 1994/14045 A1 | 6/1994 |
| WO | 2007/093670 A1 | 8/2007 |

OTHER PUBLICATIONS

International Search Report dated Mar. 8, 2010.
LipiVage Brochure "Fat Harvest, Wash & Transfer System" Genesis Biosystems, (2005).
Serres Einmal-Gewebekollektor advertisement dated Jan. 19, 2011.

* cited by examiner

METHOD AND DEVICE FOR ISOLATING TISSUE CELLS FROM A LIQUID

This application is a 371 application of PCT/DE2009/000776 filed May 29, 2009 which claims foreign priority benefit under 35 U.S.C. § 119 of German application No. 102008027486.0 filed Jun. 10, 2008.

The invention relates to a method, wherein a mixture from the tissue cells and the liquid is entrained in a vacuum flow and then again separated from the vacuum flow in a tissue collection container, wherein the tissue cells are filtered out of the mixture by gravity and the remaining liquid is again entrained in the vacuum flow.

The invention also relates to a device for separating tissue cells from a liquid, including a tissue cell collector under vacuum with a filter unit which divides the collection container into a lower collection space for the liquid, an center collection space for the tissue cells and an upper vacuum space, wherein the lower collection space for the liquid and the upper vacuum space are connected so as to bypass the collection space for the tissue cells. Such methods and devices are used in medical technology.

It is known from many areas of human medicine to remove tissue cells from a human body, for example to discard them because they are surplus, or to reprocess them because they are again needed for certain reasons. Tissue parts are here mechanically separated from the biological structure in a conventional manner, which is very painful and stressful for the patient. Instead of mechanical separation, ultrasound techniques are also used for detaching tissue cells followed by suction; however, the ultrasound techniques operate uncontrolled and are therefore also very stressful for the human body. Recently, the water jet separation method has found increased acceptance, wherein the tissue cells to be removed are gently separated from the neighboring tissue cells with a defined jet of a working liquid and the tissue parts detached in this manner are suctioned off together with the working liquid and the body fluids. The suctioned-off mixture of tissue cells and liquid must then be separated again if the tissue cells are to be used again. For example, lipoid cells removed and processed for cosmetic reasons are injected again at another location of the same human body. Vital tissue cells from a biological structure, for example the liver, are propagated through division outside the human body and the grown tissue cells are later again supplied to the respective organ of a patient.

Various methods and devices are used for separating the removed tissue cells from the liquid.

For example, a conventional method and a device from the company Genesis Biosystems, Inc., Lewisville, Tex. 75067 known by the name "LipiVage" operates according to the principle of pressure filtering. The mixture of tissue cells and working fluid is here suctioned by a piston-cylinder unit and is subsequently subjected to a pressure sufficient to press the liquid out of the tissue cells. In other words, the tissue cells are pressed dry, which of course severely stresses the tissue cells, making them unusable.

To preserve the removed tissue cells as much as possible, the tissue cells and the liquid are frequently separated by sedimentation under the influence of gravity, where the lighter tissue cells settle after some time on the surface of the heavier liquid. The tissue cells are then centrifuged to separate the still adhering residual quantities of liquid from the tissue cells. This separation method is time-consuming and requires an additional centrifuge. This makes the method ends the corresponding device expensive. However, this method is also not without stress for the tissue cells, because filtration by gravity takes a long time and because centrifugal forces act on the tissue cells during the subsequent centrifugation. This causes severe damage to the tissue cells.

A method and a device from the company Serres Oy, Kurikantie 287, FIN-61850 Kauhajoki also operate according to the laws of gravity, whereby the tissue cells are filtered out of the liquid. To this end, the corresponding device is arranged in the suction channel of the water jet separation device, so that the interior space of the device is under vacuum. The device has a cylindrical strainer container with an inserted strainer basket with straining openings arranged at the lower end and the sides, which are both matched in diameter and height so as to create a lower collection space and a peripheral annular space for the working fluid. The mixture is supplied into the strainer basket at the lid, and the pure fluid is removed from the lower collection space of the strainer container at the bottom. During filtering, the tissue cells continuously precipitate in the strainer basket, whereas the vacuum flow flows past the tissue cells through the lateral annular space. For removing the filtered tissue cells, the strainer container is opened and a suction syringe is inserted, which is used to remove the tissue cells from the lowest layer.

This method is also very time-consuming and requires subsequent centrifugation. In addition, the tissue cells are also stressed in an unacceptable manner, because they are subjected to gravity during the entire process.

It is therefore an object of the invention to develop a generic method and a generic device which improves protection of the tissue cells and shortens the filtration time.

The object is solved with a method wherein the vacuum flow, which is separate inside the tissue collection container from the mixture, is temporarily interrupted for generating additional pressure acting on the mixture.

The object is solved with a device wherein the connection between the lower collection space for the liquid and the upper collection space is a closeable bypass line.

The novel method and the novel device eliminate the aforementioned disadvantages of the state-of-the-art.

First of all, the particular advantages of the novel method and of the novel device are that all pressure forces produced by the vacuum are kept away from the tissue cells. The liquid and the tissue cells are then separated solely by gravity acting on the mixture. This protects the vitality of the tissue cells. However, it is now also possible to apply additional pressure generated by the vacuum flow on the tissue cells by closing the bypass line. This is preferably done immediately before the tissue cells are removed, thereby exposing the tissue cells to this increased pressure for only a short time. By applying the additional pressure, the residual quantities of liquid are pressed out of the tissue cells. This accelerates the filtering process and obviates the need for subsequent centrifuging.

In a particularly advantageous embodiment of the method, the liquid residing in the collection space is accumulated so that its level is located above the filter disk. The lowest layer of tissue cells is then in continuous contact with the liquid. As a result, buoyancy forces are created in the liquid which affect the lower tissue cells and oppose the force of gravity from the tissue cells. When filtering by gravity alone, the tissue cells are barely stressed, so that tissue cells of high quality can be harvested.

During the combined gravity/pressure filtering with closed bypass line, the buoyancy forces generated in the liquid oppose gravity and the vacuum forces, thereby preventing the lowest layers of the tissue cells to solidify immediately on the filter disk, which improves the permeability of the filter disk. The liquid can then more easily drip off, without subjecting the tissue cells to more stress. Advantageous embodiments are recited in the dependent claims 2, 3 and 5 to 9.

The invention will now be described in more detail with reference to an exemplary embodiment.

Figure 1:
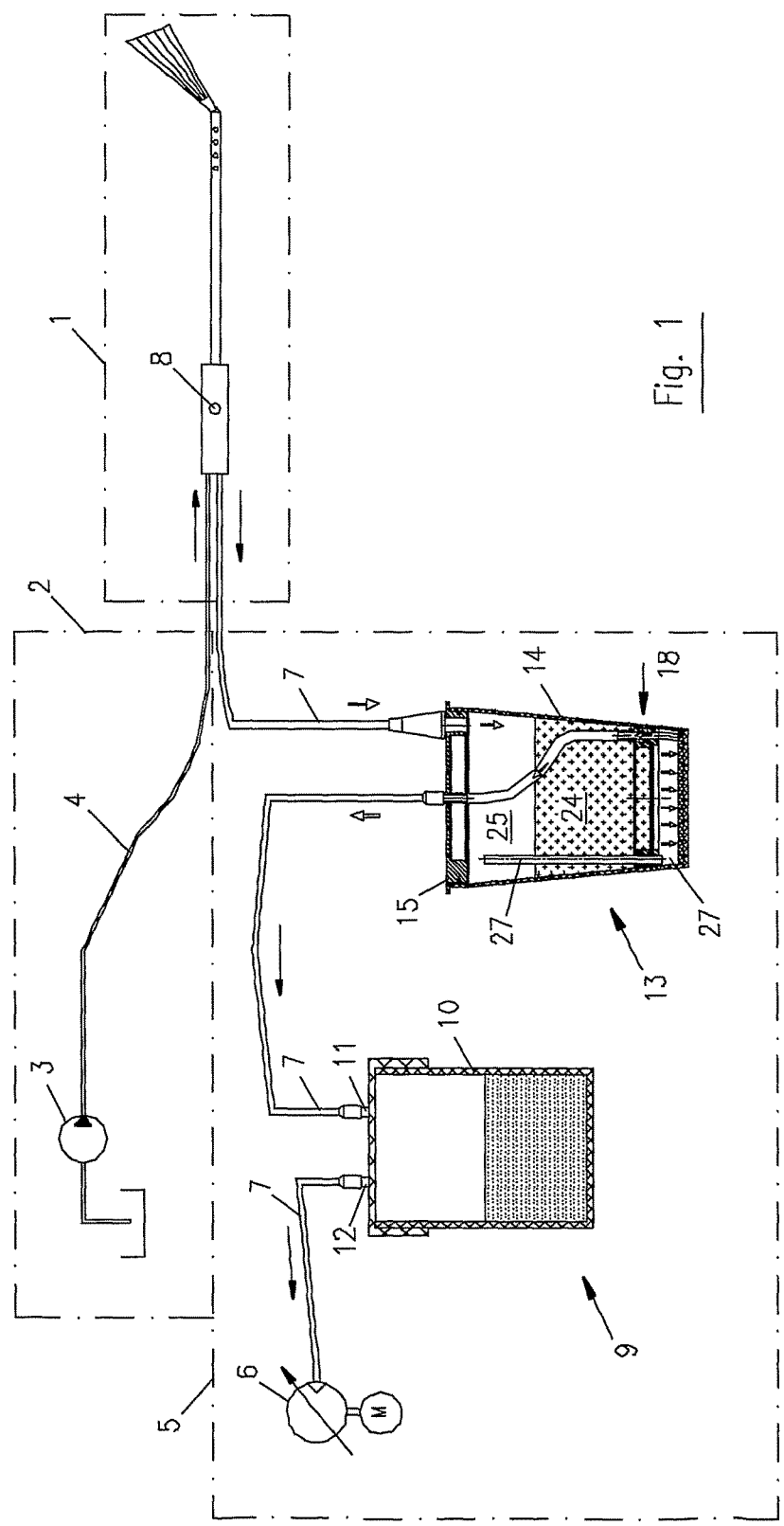
FIG. 1 shows a schematic diagram of a device for water jet separation.

According to FIG. 1, a conventional device for water jet separation includes an applicator 1 operated manually by an operator for water jet-supported separation and suctioning of tissue cells from a biological structure, a pressurized jet device 2 with a pressure generator 3 and a pressure line 4 for supplying the applicator 1 with a defined liquid jet, as well as a suction device 5 for removing the separated tissue parts and the used working liquid and the body fluid from the applicator 1. The suction device 5 includes a vacuum generator 6 and a suction line 7, wherein the suction line 7 contiguously connects the vacuum generator 6 with the applicator 1. The suction line 7 has in the region of the applicator 1 a closable bypass 8 connecting the suction line 7 with atmosphere. Disposed in the suction line 7 is first a residual liquid collector 9 for the suctioned-off liquid with a closable collection container 10, and an inlet fitting 11 and an outlet fitting 12 for the suction line 7. The residual liquid collector 9 for the filtered-out liquid is arranged before the vacuum generator 6, as viewed in the suction direction. A tissue cell collector 13 is disposed in front of the residual liquid collector 9, as viewed in the suction direction, for the liquid and in close proximity to the applicator 1.

Figure 2:
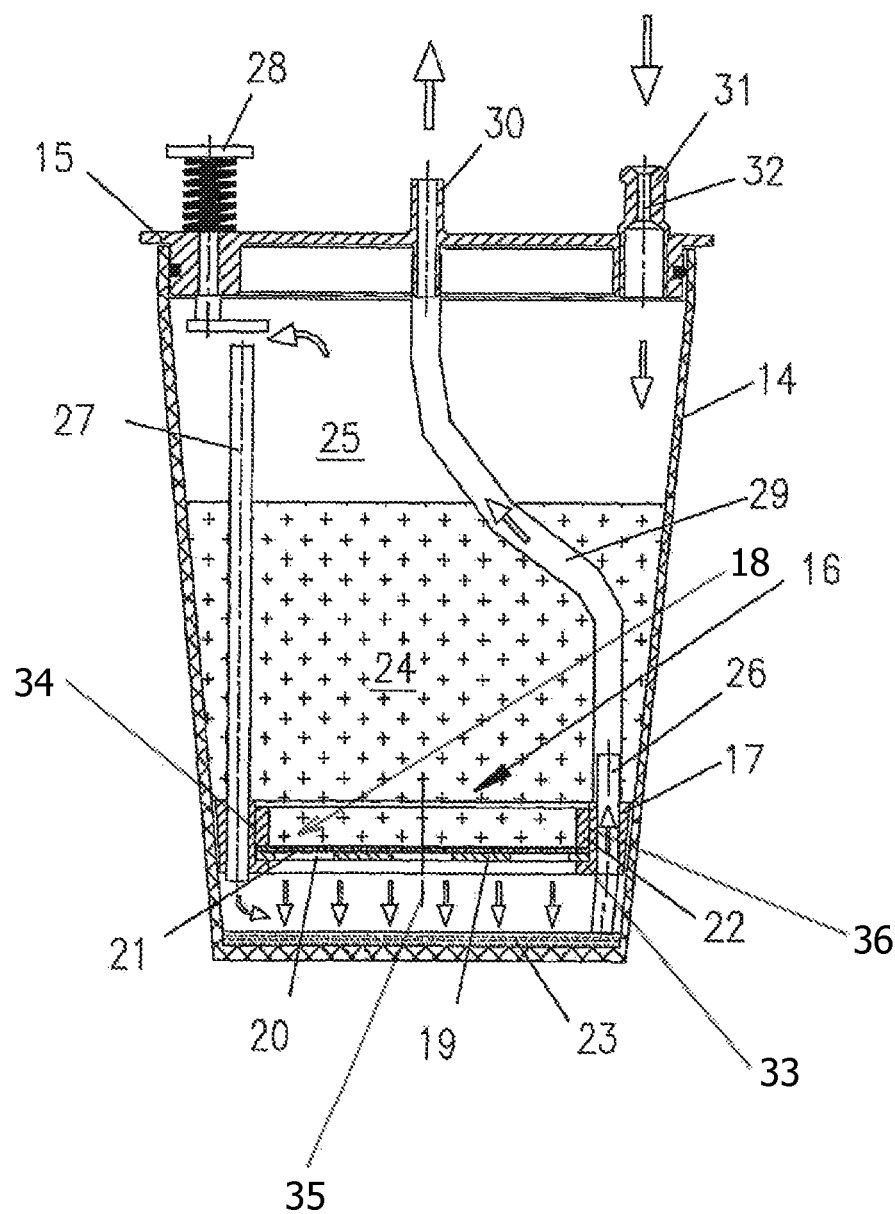
FIG. 2 shows a device for separating tissue cells from a liquid in a first embodiment.

In a first embodiment according to FIG. 2, this tissue cell collector 13 is constructed of a cylindrical collection container 14 which can be sealed pressure-tight with a lid 15. The collection container 14 is preferably cylindrical, with a conical taper towards the bottom of the collection container 14. Preferably, the collection container 14 is transparent to allow observation of the fill level and evaluation of the condition of the collected tissue cells. The collection container 14 has a fill level indicator for observing the fill level. A filter insert 16 is disposed in the collection container 14. This filter insert 16 has a support ring 17 with an outside diameter that is matched to the inside diameter of the collection container 14, so that the filter insert 16 is supported on the conical wall of the collection container 14 at a predetermined distance from the bottom of the collection container 14, thereby assuming a fixed position. The interior diameter of the support ring 17 is stepped, providing a shoulder for a filter unit 18. This filter unit is constructed of a stable bottom support disk 19 with large-area openings 20, one or more filter disks 21 with predetermined filter openings, and a top retaining ring 22. In this arrangement, the retaining ring 22 presses the filter disk 21 and the support disk 19 against the shoulder of the filter unit 18, either by its own weight or by way of clamping forces or by a positive fit with the support ring 17. The top retaining ring 22 is constructed so that it can be easily removed for changing the filter disk 21 and that it can be installed at different heights in order to adapt to the different thicknesses of the one or more filter disks 21.

By arranging the filter insert 16 at a predetermined height, a lower collection space 23 for the liquid is created below the filter insert 16 and a collection space 24 for the tissue cells is created about the filter insert. The capacity of the collection container 14 of the tissue cell collector 13 is selected so as to form a vacuum space 25 for the tissue cells above the collection space 24.

A vertically oriented suction fitting 26 and an opposite, likewise vertically oriented bypass line 27 extends through the support ring 17 of the filter insert 16. The bypass line 27 terminates at a predetermined distance below the lid 13 and thus connects the lower collection space 23 for the liquid with the upper vacuum space 25 independent of the fill level of the collection space 24 for the tissue cells. The upper opening of the bypass line 27 is constructed to be closable. For this purpose, a closure element 28 is disposed in the lid 15 of the collection container 16. This closure element 28 is spring-loaded and manually operated. In a simpler structure which is more difficult to operate, the bypass line 27 can also be directly closed manually by the operator after opening the lid 15.

The suction fitting 26 terminates below the filter insert 16 and thus determines the level of the liquid in the collection space 23. A free space separating the liquid from the tissue cells is thereby created between the collection space 23 for the liquid and the collection space 24 for the tissue cells. Towards the top, the suction fitting 26 is connected via a suction line 29 with an outlet fitting 30 located in the lid 15 of the tissue cell collector 13. The suction line 29 is preferably a hose. Also arranged in the lid 13 of the collection cell collector 13 is an inlet fitting 31 which terminates in the vacuum space 25. This inlet fitting 31 is equipped with a constant flow reducer 32. This flow reducer 32 is dimensioned so that, on one hand, atmospheric pressure can only slowly enter the suction region of the suction device 5 on the tissue cell collector 13 when the bypass 8 is open and, on the other hand, flow of the mixture of tissue cells and liquids is not greatly hindered.

The support ring 17 comprises first inner surfaces 34 adjacent to the lower portion of the bypass line 27 facing inward towards a center axis 35 of the collection container 14, that runs parallel to the bypass line 27 and second inner surfaces 36 adjacent to the lower portion of the suction line 29 facing inward towards the center axis 35 of the collection container. A first plane extends downwardly from, and is defined by, the first inner surfaces 34 at the lower portion of the bypass line 27 and a second plane extends downwardly from, and is defined by, the second inner surfaces 36 at the lower portion of the suction line 29. At least a portion of the filter unit 18 contacts the first inner surfaces 34 of the support ring 17 adjacent to the bypass line 27 and the second inner surfaces 36 of the support ring 17 adjacent to the suction line 29. The filter unit 18, in its entirety, is disposed between the first plane 37 and the second plane 38.

Figure 3:
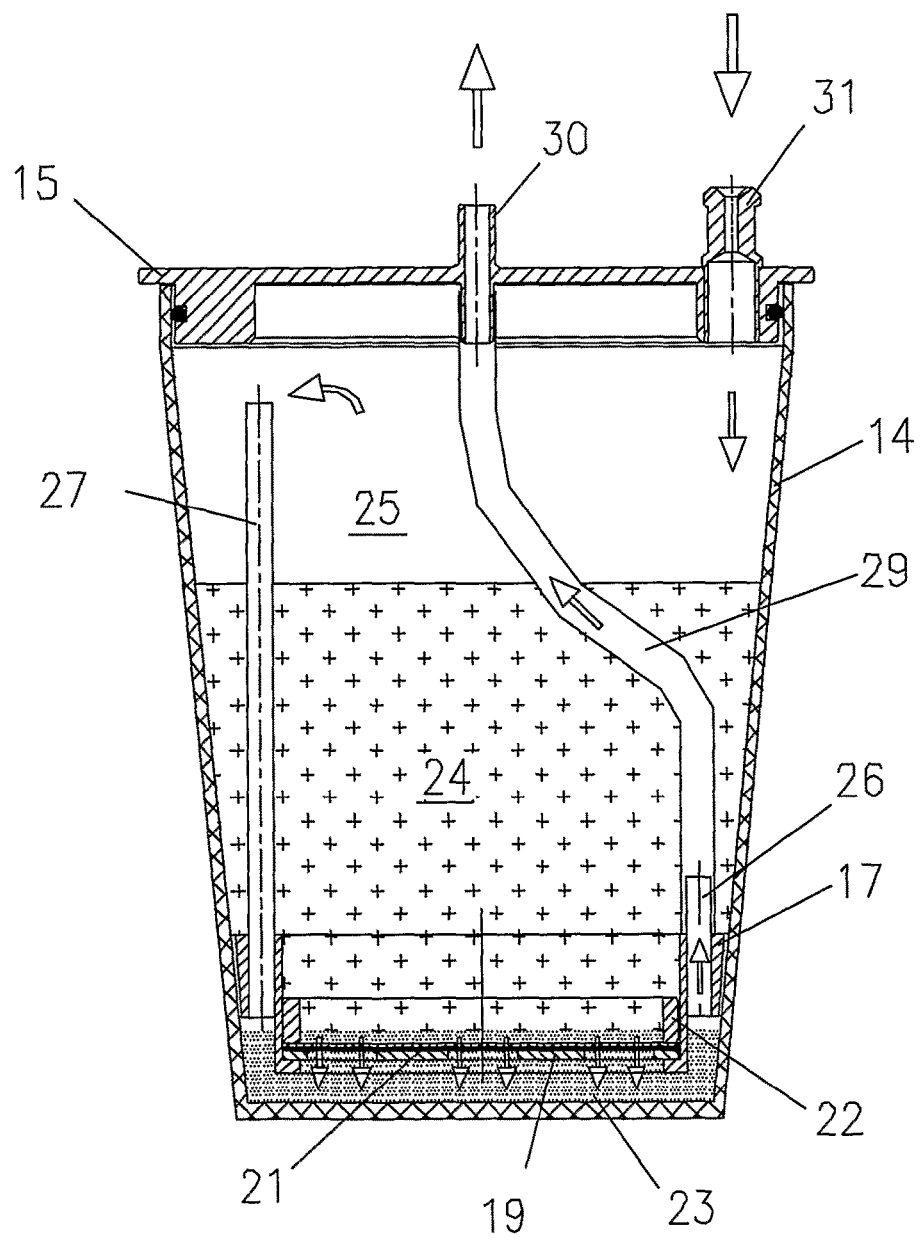
FIG. 3 shows a device for separating tissue cells from a liquid in a second embodiment.

In the second embodiment according to FIG. 3, the tissue cell collector 13 is different from the first embodiment in that the closure element 28 has been omitted and the filter insert 16 is constructed differently. The suction fitting 26 is particularly constructed so that the lower outlet opening of the suction fitting 26 is located at a height which is higher by a predetermined amount than the height of the filter disk 21, so that the liquid level of the working liquid disposed in the collection space 23 rises above the filter disk 21 by the predetermined amount.

The device has the following function.

When using the water jet separation method, a defined liquid separation jet exits the applicator 1, wherein the effect of the liquid separation jet is determined by the liquid pressure generated in the pressure jet device and the construction of the applicator 1. This effect is intended to gently separate the tissue cells from a biological structure. The tissue cells separated in this way are suctioned off together with the injected working liquid and the additional body fluids by a vacuum generated in the suction device 5. This method is frequently used with liposuction.

In situations where the suctioned tissue cells are to be reused, these tissue cells are filtered from the tissue cell-liquid mixture. This is done by the tissue cell collector 13.

In the standby position, the operator holds the closable bypass 8 open, so that no suction occurs, but only air from the atmosphere is suctioned in and transported through the tissue cell collector 13. The restricted air flow passes the inlet fitting 31 and reaches through both the bypass line 27 and the exposed filter unit 18 the lower collection space 23 for the liquid, from where the air flows through the suction line 29 to the outlet fitting 30.

In the operating position, the closable bypass 8 is closed by the operator, so that the suction from the vacuum generator 6 is transferred to the operating field. The separated tissue parts and the different liquids are then entrained and transported to the tissue cell collector 13.

In the tissue cell collector 13 of the first embodiment according to FIG. 2, the mixture off tissue cells and the liquid flows through the inlet fitting 31 into the tissue cell collector 13 and on the filter insert 16. The liquid then drips through the filter disk 21 by gravity and is collected in the collection space 23. The tissue cells are held back by the filter disks 21, where they deposit. At the same time, the vacuum flow is directed through the bypass line 27 and—mostly past the deposited tissue cells—into the lower collection space 23 for the liquid. The vacuum flow entrains the accumulated liquid and transports it through the suction fitting 26 and the suction line 29 to the outlet fitting 30. To accelerate the filtering process produced by gravity, the operator closes the bypass line 27 briefly with the closure element 28. The flowing vacuum flow is then switched off, so that the vacuum flow must find its way only through the tissue cells that have accumulated in the meantime. The generated forces assist gravity and press the residual quantities of the liquid out of the tissue cells. This combined gravity-pressure filtration accelerates the filtering process. The time during which the tissue cells are exposed to the vacuum forces is kept short and performed as close as possible to the removal of the tissue cells, in order to not unnecessarily stress the tissue cells. The liquid that is transported away is then separated from the vacuum flow in the residual liquid collector 9 and disposed of.

The tissue cell collector 13 of the second embodiment according to FIG. 3 operates in the same way. However, due to the greater height of the outlet opening of the suction fitting 26 and the lower height of the filter disk 21, the level of the accumulated liquid is located above the filter disk 21, so that the lower layer of the tissue cells is in constant contact with the liquid. The buoyancy forces of the liquid oppose the force of gravity of the tissue cells and the pressure forces of the vacuum flow, thereby lessening stress to the tissue cells.

LIST OF REFERENCES SYMBOLS

1 Applicator
2 Pressure jet device
3 Pressure generator
4 Pressure line
5 Suction device
6 Vacuum generator
7 Suction line
8 Closable bypass
9 Residual liquid collector
10 Collection container
11 Inlet fitting
12 Outlet fitting
13 Tissue cell collector
14 Collection container for the tissue cells
15 Lid
16 Filter insert
17 Support ring
18 Filter unit
19 Support disk
20 Opening
21 Filter disk
22 Retaining ring
23 Collection space for the liquid
24 Collection space for the tissue cells
25 Vacuum space
26 Suction fitting
27 Bypass line
28 Closure element
29 Suction line
30 Outlet fitting
31 Inlet fitting
32 Constant flow restrictor
33 Shoulder
34 First inner surface
35 Center axis
36 Second inner surface

The invention claimed is:

1. A device for separating tissue cells from a liquid, comprising a tissue cell collector under vacuum with a filter insert which divides a collection container for the tissue cells into a lower collection space for the liquid, a center collection space for the tissue cells and an upper vacuum space, wherein the lower collection space for the liquid and the upper vacuum space feature a bypass line bypassing the center collection space for the tissue cells, wherein the device comprises a suction line, extending separately from the bypass line, from the lower collection space for the liquid to an outlet fitting of the tissue cell collector, wherein the filter insert comprises a support ring and a filter unit and is disposed in the collection container, wherein the filter unit comprises one or more filter disks and is positioned against a shoulder of the support ring, wherein the bypass line has a bypass line length defined between an upper portion and a lower portion of the bypass line and the suction line has a suction line length defined between an upper portion and a lower portion of the suction line, wherein the support ring comprises first inner surfaces adjacent to the lower portion of the bypass line facing inward towards a center axis of the collection container, that runs parallel to the bypass line and second inner surfaces adjacent to the lower portion of the suction line facing inward towards the center axis of the collection container, wherein a first plane extends downwardly from the first inner surfaces at the lower portion of the bypass line and a second plane extends downwardly from the second inner surfaces at the lower portion of the suction line, wherein at least a portion of the filter unit contacts the first inner surfaces of the support ring adjacent to the bypass line and the second inner surfaces of the support ring adjacent to the suction line, and further wherein the filter unit, in its entirety, is disposed between the first plane and the second plane.

2. The device according to claim 1, wherein the bypass line is closable by a closure element.

3. The device according to claim 1, wherein the collection container is cylindrical with a conical taper towards a bottom end of the collection container.

4. The device according to claim 2, wherein the closure element is a spring-loaded closure element.

5. The device according to claim 1, wherein the collection container is configured such that liquid, when present in the center collection space, is passable from the center collection space to the lower collection space via the filter unit.

6. The device according to claim 1, wherein the outlet fitting is located adjacent to the upper portion of the suction line and a suction fitting is located adjacent to the lower portion of the suction line.

7. The device according to claim 1, wherein the center collection space for the tissue cells is penetrated by the suction line, wherein the outlet fitting is arranged in a lid of the tissue cell collector.

8. The device according to claim 1, wherein the one or more filter disks is arranged at a height below an outlet opening of a suction fitting for the suction line.

9. The device according to claim 8, wherein the tissue cell collector is configured such that tissue cells, when present in the collection container, are collectible in the center collection space.

10. The device according to claim 1, wherein the one or more filter disks of the filter insert is horizontally positioned between the lower portions of the bypass and suction lines.

11. The device according to claim 1, wherein the bypass line and the suction line terminate at the lower portions that are adjacent to a bottom side or end of the tissue cell collector when the device is located in an upright position.

12. The device according to claim 1, wherein the filter unit, in its entirety, is arranged horizontally between the lower portions of the bypass and suction lines.

* * * * *